| United States Patent [19] | [11] 4,208,424 |
| Carr | [45] Jun. 17, 1980 |

[54] LIPOGENESIS INHIBITION BY CERTAIN ESTERS OF SUBSTITUTED BENZODIOXINCARBOXYLIC ACIDS

[75] Inventor: John B. Carr, Houston, Tex.

[73] Assignee: Shell Oil Company, Houston, Tex.

[21] Appl. No.: 33,636

[22] Filed: Apr. 26, 1979

[51] Int. Cl.² ............................................. A61K 31/335
[52] U.S. Cl. ................................. 424/278; 260/340.3
[58] Field of Search ...................... 424/278; 260/340.3

[56] References Cited

U.S. PATENT DOCUMENTS

| 3,777,017 | 12/1973 | McGovern et al. .......... 260/340.3 X |
| 4,103,021 | 7/1978 | Carr ..................................... 424/278 |
| 4,118,507 | 10/1978 | Carr ..................................... 424/278 |

Primary Examiner—Ethel G. Love

[57] ABSTRACT

Use as lipogenesis inhibitors in mammals of alkyl esters of certain substituted 2,3-dihydro-1,4-benzodioxincarboxylic acids.

1 Claim, No Drawings

LIPOGENESIS INHIBITION BY CERTAIN ESTERS OF SUBSTITUTED BENZODIOXINCARBOXYLIC ACIDS

DESCRIPTION OF THE INVENTION

It has been found that lipogenesis in mammals is inhibited by alkyl esters of certain substituted 2,3-dihydro-benzodioxin-2-carboxylic acids, of the formula

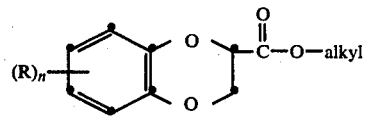

wherein "alkyl" is straight-chain or branched-chain alkyl of from one to four carbon atoms, and the substituent moiety or moieties, R, are as follows, the number(s) preceding the moieties indicating the position of each of said moieties on the ring:

| Species No. | $(R)_n$ |
|---|---|
| 1 | H (n = zero) |
| 2 | mixture of the 6- and 7-methyl isomers (n = 1) |
| 3 | mixture of the 6- and 7-fluoro isomers (n = 1) |
| 4 | mixture of the 6- and 7-bromo isomers (n = 1) |
| 5 | mixture of the 5- and 8-methoxy isomers (n = 1) |
| 6 | 6,7-dimethyl (n = 2) |
| 7 | 6-phenyl (n = 1) |
| 8 | 7-phenyl (n = 1) |
| 9 | 7-(hydroxyethyl) (n = 1) |
| 10 | mixture of the 6- and 7-methoxy isomers (n = 1). |

Chirality exists in the compounds of Formula I due to the asymmetric structural configuration at the 2-position of the 2,3-dihydro-1,4-benzodioxin ring. As a result, each of these compounds exists in the forms of two optical isomers. The individual isomers have not been separated, so that their respective activity as lipogenesis inhibitors has not been determined. The invention contemplates each of the individual active isomers, as well as racemic, and other mixtures thereof.

Preparation of individual species of the compounds of Formula I is illustrated in the following examples, the individual species in each case being the ethyl ester.

In each of these examples, the identities of the products, and the intermediates involved, were confirmed by appropriate elemental and spectral analyses.

EXAMPLE 1

Ethyl 2,3-dihydro-1,4-benzodioxin-2-carboxylate (1)

Prepared as a liquid, bp: 100°–103° C. (0.01 Torr.) by the method of Koo, et al., J. Am. Chem. Soc., 77, 5373–5 (1955).

EXAMPLE 2

Ethyl 2,3-dihydro-6(and 7)-methyl-1,4-benzodioxin-2-carboxylate (2)

15 g of ethyl 2,3-dibromopropionate was added slowly to a stirred refluxing mixture of 24.8 g of 4-methylcatechol, 23 g of potassium carbonate and 250 ml of acetone. In three additional increments was added over a one-hour period: 20 g of potassium carbonate and 27.2 g of ethyl 2,3-dibromopropionate. The mixture then was refluxed for 6 hours and allowed to stand over a weekend. The mixture then was filtered, the solids were washed with acetone, the solvent was stripped from the combined filtrate and washings and the residue was vacuum distilled to give a mixture of the ethyl esters of 2,3-dihydro-6-(and 7-)-methyl-1,4-benzodioxin-2-carboxylic acids (2), bp: 124°–126.5° C. (0.045 Torr.).

EXAMPLE 3

Ethyl 2,3-dihydro-6(and 7)-fluoro-1,4-benzodioxin-2-carboxylate (3)

26 g of 4-fluorocatechol (prepared by the procedure of Corse, J., et al., J. Org. Chem., 16, 1345 (1951)) was mixed with 57 g of ethyl 2,3-dibromopropionate, 82 g of potassium carbonate and 300 ml of acetone at 15° C., the temperature of the mixture being allowed to rise over a 2-hour period to 25° C. The mixture then was refluxed for 3.5 hours, cooled and filtered. The filtrate was stripped of solvent to give a paste, which was filtered. The filtrate was treated with water and methylene chloride. The methylene chloride phase was separated and stripped of solvent, and the residue was vacuum distilled to give a mixture of the ethyl esters of 2,3-dihydro-6-(and 7)-fluoro-1,4-benzodioxin-2-carboxylic acids (3), bp: 116°–120° C. (0.1 Torr.).

EXAMPLE 4

Ethyl 6(and 7)-bromo-2,3-dihydro-1,4-benzodioxin-2-carboxylate (4)

90 g of ethyl 2,3-dibromopropionate in 500 ml of acetone was added to a stirred suspension of 193 g of potassium carbonate and 122 g of 4-bromocatechol (prepared by brominating catechol according to the procedure of Yanovskaya, et al., Zhur. Obschei. Khim. (J. Gen. Chem.), 22, 1954 (1952) (Chem. Abst. 46, 6095b)) in 500 ml of acetone. The temperature of the mixture rose to 35° C. The mixture was heated at about 50° C. for 6.5 hours. The mixture was cooled and filtered and the solvent was evaporated from the filtrate. The residue was taken up in a mixture of water and hexane. The hexane phase was separated, the hexane was evaporated, and the residue was vacuum distilled to give a mixture of isomers of the ethyl esters of 6-(and 7-)-bromo-2,3-dihydro-1,4-benzodioxin-2-carboxylic acids (4), bp: 140°–145° C., (0.1 Torr.).

EXAMPLE 5

Ethyl 2,3-dihydro-8(and 5)-methoxy-1,4-benzodioxin-2-carboxylate (5)

51.5 g of ethyl 2,3-dibromopropionate was added drop-by-drop over a 40-minute period to a stirred, refluxing mixture of 25 g of 3-methoxycatechol, 74.5 g of potassium carbonate and 250 ml of dry acetone. The mixture was refluxed for 17 hours, cooled and filtered. The solvent was evaporated from the filtrate under reduced pressure. The residue was taken up in methylene chloride. The solution was washed with water, dried (MgSO$_4$) and vacuum distilled to give 5, bp: 150°–155° C. (0.02–0.05 Torr.).

EXAMPLE 6

Ethyl 2,3-dihydro-6,7-dimethyl-1,4-benzodioxin-2-carboxylate (6)

53 g of 4,5-dimethylveratrol (prepared by the method of Bruce, et al., J. Chem. Soc., 1956, 3824–29) was mixed with 200 ml of 48% hydrobromic acid. The mixture was stirred at reflux temperature, in a nitrogen atmosphere, for 4.5 hours. The crude mixture was heated with 200 ml of toluene. The toluene phase was separated and cooled, to give 4,5-dimethylcatechol (6A), as a solid, mp: 86°–87° C.

86 g of ethyl 2,3-dibromopropionate was added, over a 15-minute period, to a stirred mixture of 41 g of 6A, 97 g of potassium carbonate and 300 ml of acetone. The temperature of the mixture rose to 60° C. The mixture was refluxed for 19 hours, cooled to 30° C. and filtered. The solvent was evaporated from the filtrate under reduced pressure. The residue was recrystallized from hexane to give 6, mp: 71°–72° C.

EXAMPLE 7

Ethyl 2,3-dihydro-6-phenyl-1,4-benzodioxin-2-carboxylate (7)

46.1 g of ethyl 2,3-dibromopropionate was added slowly to a mixture of 30 g of 4-phenylcatechol, 66.2 g of potassium carbonate, and 250 ml of acetone. The mixture was refluxed for 18 hours, cooled and filtered. The solvent was evaporated from the filtrate under reduced pressure. The residue was extracted with hot cyclohexane. The extract was dried ($MgSO_4$) and filtered. The solvent was evaporated from the filtrate under reduced pressure. The residue was taken up in hexane/methylene chloride. The solution was cooled. The resulting solid (7A) was separated and recrystallized from cyclohexane to give 7, mp: 103°–105° C.

EXAMPLE 8

Ethyl 2,3-dihydro-7-phenyl-1,4-benzodioxin-2-carboxylate

The mother liquor from which 7A was separated was stripped of solvent under reduced pressure. The residue was dissolved in warm cyclohexane. The solution was cooled to give white crystals, which were separated, and taken up in cyclohexane. The solution was filtered. The mother liquor was cooled to give two crops of solid ((a) mp: 64°–71° C.; (b) 78°–81° C.). Crop (b) was taken up in cyclohexane and cooled to give 8 as a solid, mp: 67°–69° C.

EXAMPLE 9

Ethyl 2,3-dihydro-7-(1-hydroxyethyl)-1,4-benzodioxin-2-carboxylate (9)

400 ml of a mixture of 1:8 v/v glacial acetic acid in water was added in two portions to a stirred mixture of 35 g of 4-(chloroacetyl)catechol in 300 ml of ethanol. At 10 minute intervals, four 10 g portions of 90% zinc dust were added, the mixture being held below about 45° C. The mixture then was stirred for 2 hours at 30°–40° C. and allowed to stand over a weekend. The liquid phase was decanted and stripped to a quarter of its volume under reduced pressure. The remaining mixture was extracted with ether, the extract was washed with sodium bicarbonate solution. The solvent was evaporated. The solid residue was recrystallized from toluene to give 4-acetylcatechol (9A), mp: 118°–119° C.

150 g of ethyl 2,3-dibromopropionate was added over a 3-hour period to a stirred slurry of 96 g of 9A, 234 g of potassium carbonate and 600 ml of acetone. The temperature of the mixture rose from 23° C. to 40° C. The mixture then was refluxed (55° C.) for 19 hours, and filtered. The acetone was evaporated from the filtrate under reduced pressure. The residue was distilled to give a mixture of the ethyl esters of 7-(and 6-)-acetyl-2,3-dihydro-1,4-benzodioxin-2-carboxylic acids (9B), as a colorless liquid, bp: 165°–166° C. (0.1 Torr).

5.7 g of sodium borohydride was added to a stirred mixture of 60 g of 9B and 1200 ml of ethanol. The mixture was stirred at room temperature for 3 hours, and stored overnight. The mixture was acidified to a pH of 3–4 by the addition of 110 ml of 3.5% hydrochloric acid, and filtered. The solvent was evaporated from the filtrate under reduced pressure. The residue was suspended in a mixture of 300 ml of water and 300 ml of ether. The organic phase was separated, dried ($MgSO_4$) and the solvent was evaporated under reduced pressure. The residue was chromatographed over silica gel using ether as eluent. The appropriate fractions were combined and the solvent was evaporated under reduced pressure. The resulting oil was diluted with ether and the mixture was filtered. The solvent was evaporated under reduced pressure and the residue was chromatographed over silica gel using ether as eluent. The appropriate fractions were combined and the solvent was evaporated under reduced pressure to give 9, as a liquid, boiling point not determined.

EXAMPLE 10

Ethyl 2,3-dihydro-6(and 7)-methoxy-1,4-benzodioxin-2-carboxylate (10)

4-methoxycatechol was prepared by the method described in Organic Synthesis, Collective Volume 3, page 759: 60.8 g of 4-methoxysalicylaldehyde was added to a stirred solution of 16 g of sodium hydroxide in 200 ml of water. Under nitrogen gas, a solution of 60 g of 30% hydrogen peroxide in water dissolved in 200 ml of water was added drop-by-drop to the resulting solution, held at 35°–40° C. Then sodium sulfate (and a small amount of sodium hydrosulfite to decolorize the mixture) was added until the mixture was saturated. The mixture was extracted with methylene chloride. The resulting residue was extracted with ether. The ether extract was dried ($Na_2SO_4$, $Na_2S_2O_4$) and the solvent was evaporated under reduced pressure, to give crude 4-methoxycatechol (10A).

102 g of ethyl 2,3-dibromopropionate was added drop-by-drop over a 2-hour period to a stirred mixture of 55 g of 10A, 130 g of potassium carbonate and 400 ml of acetone. The mixture was refluxed for 16 hours, then filtered. The solvent was evaporated from the filtrate under reduced pressure and the residue was distilled to give 10, bp: 138°–139° C. (0.1 Torr.).

Esters of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical for a period of time, then isolating the lipid from the treated tissue and determining the incorporation of the radioactive carbon into lipid by means of scintillation counting techniques. These tests were conducted in swine adipose tissues because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-$U^{14}C$, and 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform/methanol (2:1 v/v). The extracts were washed according to Folch et al. (J. Biol. Chem. 226, 497–509, (1957)), air dried, and counted in a liquid scintillation counter with 15 m milliliters of counting fluid (two parts toluene containing 0.4% w/v New England Nuclear Omnifluor/1 part Triton X-100). The tests were conducted in triplicate and were accompanied by control tests in which all ingredients, proportions and conditions were the same except that no test compound was included. From the data obtained were calculated the percent inhibition of lipid synthesis by the test compounds in each case. The data obtained from the tests are set out in Table 1, as the percent inhibition of lipogenesis compared to the results obtained in the control tests wherein only the test compound was omitted.

Table I

| Compound No. | Percent Inhibition |
| --- | --- |
| 1 | 22 |
| 2 | 30 |
| 3 | 48 |
| 4 | 43 |
| 5 | 86 |
| 6 | 29 |
| 7 | 21 |
| 8 | 28 |
| 9 | 90 |
| 10 | 85 |

The esters of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the esters orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parental administration, they may be in the form of a solution, suspension, dispersion or emulsion. They can be administered in the form of an implant or other controlled sustained release formulation. Inert carriers, such as one or more of water, edible oil, gelatin, lactose, starch, magnesium sterate, talc or vegetable gum can be used. The dosage of the ester needed to inhibit lipogenesis will depend upon the particular ester used, and the particular animal being treated. However, in general, satisfactory results are obtained when the esters are administered in a dosage of from about 1 to about 400 milligrams per kilogram of the animal's body weight. The ester can be administered in a single dose or in a series of doses in the same day, or over a period of days. For any particular animal, a specific dosage regimen should be adjusted according to the individual need, the particular ester(s) used as the inhibitor, and the professional judgment of the person administering or supervising the administration of the inhibitor. It is to be understood that the dosages set forth herein are exemplary only, and that they do not, to any extent, limit the scope or practice of the invention.

I claim as my invention:

1. A method of inhibiting lipogenesis in a mammal, which comprises administering, to a mammal in need of such treatment, orally or parenterally a lipogenesis inhibiting amount of a compound of the formula

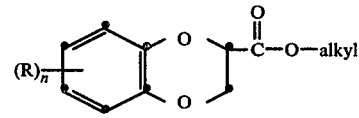

wherein "alkyl" is alkyl of from one to four carbon atoms, and the substituent moiety or moieties, R, are as follows, the number(s) preceding the moieties indicating the position of each of said moieties on the ring:

| Species No. | $(R)_n$ |
| --- | --- |
| 1 | H (n = zero) |
| 2 | mixture of the 6- and 7-methyl isomers (n = 1) |
| 3 | mixture of the 6- and 7-fluoro isomers (n = 1) |
| 4 | mixture of the 6- and 7-bromo isomers (n = 1) |
| 5 | mixture of the 5- and 8-methoxy isomers (n = 1) |
| 6 | 6,7-dimethyl (n = 2) |
| 7 | 6-phenyl (n = 1) |
| 8 | 7-phenyl (n = 1) |
| 9 | 7-(hydroxyethyl) (n = 1) |
| 10 | mixture of the 6- and 7-methoxy isomers (n = 1). |

* * * * *